United States Patent [19]

Bezwada et al.

[11] Patent Number: 4,532,928

[45] Date of Patent: Aug. 6, 1985

[54] SURGICAL SUTURES MADE FROM ABSORBABLE POLYMERS OF SUBSTITUTED BENZOIC ACID

[75] Inventors: Rao S. Bezwada, Whitehouse Station; Shalaby W. Shalaby, Mountainville; Dennis D. Jamiolkowski, Long Valley, all of N.J.

[73] Assignee: Ethicon, Inc., Somerville, N.J.

[21] Appl. No.: 627,933

[22] Filed: Jul. 5, 1984

Related U.S. Application Data

[62] Division of Ser. No. 459,428, Jan. 20, 1983.

[51] Int. Cl.³ .................................................. A61K 17/00
[52] U.S. Cl. .................................. 128/335.5; 528/173; 528/176; 528/193; 528/194; 528/206; 528/271
[58] Field of Search ...................... 128/335.5; 528/206, 528/176, 193, 194, 271, 173

[56] References Cited

U.S. PATENT DOCUMENTS

| | | | |
|---|---|---|---|
| 4,140,678 | 2/1979 | Shalaby et al. | 128/335.5 |
| 4,201,216 | 5/1980 | Mattei | 128/335.5 |
| 4,224,946 | 9/1980 | Kaplan | 128/335.5 |
| 4,300,565 | 11/1981 | Rosensaft et al. | 128/335.5 |

*Primary Examiner*—Lester L. Lee
*Attorney, Agent, or Firm*—Charles J. Metz

[57] ABSTRACT

Absorbable, radiation sterilizable polymers, useful as sutures and other medical and surgical devices, are produced from polyesters of substituted benzoic acid, dihydric alcohols, and glycolide and/or lactide.

23 Claims, No Drawings

SURGICAL SUTURES MADE FROM ABSORBABLE POLYMERS OF SUBSTITUTED BENZOIC ACID

This application is a division of our application Ser. No. 459,428, filed on Jan. 20, 1983.

The invention relates to certain polymers and to the valuable surgical products that can be made therefrom.

BACKGROUND OF THE INVENTION

Synthetic absorbable polymers have been used to produce various surgical products such as sutures, implants, prostheses, and the like, for several years. Illustrative U.S. patents that disclose such polymers are U.S. Pat. Nos. 3,297,033, 3,044,942, 3,371,069, 3,531,561, 3,636,956, RE 30,170, and 4,052,988.

Implantable surgical devices must be sterile prior to implanting in the body. Sterilization of devices is usually accomplished by the use of heat, ethylene oxide, or gamma radiation using a $^{60}$Co source. In many cases, the use of gamma radiation is the most convenient and most certain way to effect sterilization. However, all of the synthetic absorbable polymers now in commercial use are significantly degraded by gamma radiation. Therefore, unless for some reason degradation of the polymer is desired (for instance, to greatly accelerate the absorption rate), the use of gamma radiation is precluded for the purpose of sterilizing the presently commercial synthetic absorbable polymners.

This invention provides a new class of polymers that are absorbable and which can be sterilized by gamma radiation while still retaining a desirable level of physical and biological properties.

SUMMARY OF THE INVENTION

The polymers provided by the invention are derived from substituted benzoic acids and certain sulfide and sulfone analogs thereof. The base polymer from which the absorbable polymers of the invention are made is a polyester comprising repeating divalent units of the formula:

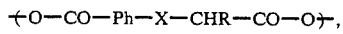  (A)

and

,  (B)

and, optionally, also

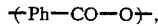,  (C)

wherein Ph represents phenylene or alkyl- or alkoxy-substituted phenylene, wherein X represents oxy, thio, or sulfonyl, wherein R represents hydrogen, lower alkyl, phenyl, or benzyl, wherein G represents the residue after removal of the hydroxyl groups of a dihydric alcohol, and wherein the divalent units (A), (B), and (C) are bonded to each other through ester groups contained in said units.

The said polyesters are reacted with a glycolide to produce the absorbable, radiation sterilizable copolyester polymers that comprise repeating divalent units of the formulas (A), (B), optionally (C), all as defined above, plus the divalent unit of the formula:

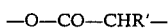  (D)

wherein R' represents hydrogen or methyl, wherein the divalent units (A), (B), (C), and (D) are bonded to each other through ester groups contained in said units.

The Prior Art

Kito et al., in Kogyo Kagaku Zasshi 1971, 74 (11), 2313-15 (CA 76, 45892c, 1972), report the preparation of ω-(p-carboxyphenoxy)alkanoic acids and their dimethyl esters.

U.S. Pat. No. 3,637,595 discloses liquid crystal copolyesters prepared from terephthalic acid, hydroquinone, and p-hydroxybenzoic acid.

British Pat. Nos. 1,507,207 and 1,508,646 (equivalent to German OS 2,520,820) disclose liquid crystal polyesters prepared from a variety of dihydric phenols and aromatic dicarboxylic acids.

In Shalaby et al., U.S. patent application Ser. No. 392,331, filed June 29, 1982 and assigned to the same assignee as this application, there is disclosed radiation sterilizable, absorbable polymers derived from 1,4-phenylene-bis-oxyacetic acid, including copolymers of poly(alkylene 1,4-phenylene-bis-oxyacetate) and polyglycolides and/or polylactides.

DETAILED DESCRIPTION OF THE INVENTION

Preparation of Monomer

In the preferred aspect of the invention wherein X in the divalent unit (A) is oxy, the convenient starting monomer, the dimethyl ester of 4-(carboxymethyoxy)-benzoic acid can be produced from methyl p-hydroxybenzoate (an article of commerce often called "methylparaben") by a straight-forward ether synthesis, as is illustrated by Example 1:

EXAMPLE 1

Preparation of Dimethyl Ester of 4-(carboxymethoxy)benzoic Acid

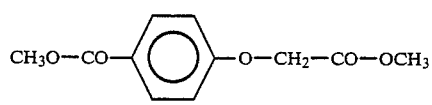

I.

152.15 Grams (1 mole) of methyl p-hydroxybenzoate, 130.22 grams (1.2 mole) of methyl chloroacetate, and 427 milliliters of anhydrous methanol are charged into a 2-liter, 3-neck, round bottom flask fitted with an addition funnel with a nitrogen inlet, a mechanical stirrer, a reflux condenser with a drying tube, a thermometer, and a heating mantle. The reaction mixture is refluxed for 30-60 minutes. A solution of sodium methoxide in methanol (216.08 grams, 25% by weight, or 1 mole of sodium methoxide) is added through the addition funnel in 1-2 hours at reflux. After the addition is completed, the reaction mixture is refluxed for about 16 hours under nitrogen. One milliliter of glacial acetic acid is added to make sure that the reaction mixture is not basic. The hot solution is then filtered to remove the precipitated sodium chloride. Upon cooling the mother liquor, white crystalline material is precipitated. The crystals are filtered, dried, and are then recrystallized twice from anhydrous methanol using 3.5 milliliters per gram of dried product. The product has a melting point of 94°-95.5° C. with an overall yield of 163 grams of the dimethyl ester of 4-(carboxymethoxy)benzoic acid (72.7%). For brevity, this compound is occasionally referred to herein as "CMB" (for "carboxymethoxy benzoate").

The corresponding 1,2- and 1,3-isomers are derived by analogous procedures from methyl salicylate and methyl m-hydroxybenzoate, respectively. In those aspects of the invention wherein R in the divalent unit (A) is phenyl, benzyl, or alkyl, a substituted alpha-chloroacetic acid ester is used in place of methyl chloroacetate. Examples includes methyl alpha-chlorobutyrate, methyl alphachloropropionate, methyl 2-chloro-2-phenylacetate, methyl 2-chloro-3-phenylpropionate, and methyl 2-chlorohexanoate.

The thio analogs, wherein X in the divalent unit (A) is thio, are prepared by the same procedure from the corresponding thiophenol, methyl p-sulfhydrylbenzoate, and methyl chloroacetate. The sulfone analog, wherein X is sulfonyl, is prepared by oxidation of the thio compound.

The benzene ring in the hydroxybenzoic acid starting reactant can contain substituent groups such as lower alkyl (e.g., methyl) or lower alkoxy (e.g., methoxy) that do not interfere with the esterification reactions to which the monomer will be subjected in producing the copolyester of the invention.

The three essential classes of reactants employed to produce the radiation-sterilizable, absorbable copolyesters of this invention are (a) carboxymethoxybenzoic acids or esters (or thio or sufonyl analogs thereof), (b) dihydric alcohols, and (c) glycolic and/or lactic acid (usually employed in the form of glycolide and/or lactide). The straightforward procedure for producing the copolyesters is to react (a) with (b) to produce a base polyester, which is then reacted with (c) to produce the copolyester. However, in some cases it may be desirable to add additional aromatic moieties in (a), or to, in effect, pre-react (a) with (b), or (a) with (c), or (a) with (b) plus (c), in order to enhance the solubility of the base polyester in the (c) reactant, or to enhance or otherwise modify the crystallinity of the copolyester, or to alter other properties of the copolyester. Thus, instead of using CMB as the starting reactant, the compounds discussed below can be employed in place of or in addition to CMB. (This principle will be illustrated with p-hydroxybenzoic acid as the starting reactant. However, it is applicable to the ortho and meta isomers and to the thio and sulfonyl analogs.)

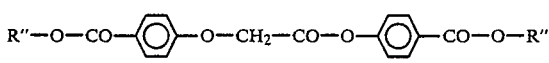

II.

wherein each R" individually is hydrogen or preferably the residue after removal of the hydroxyl groups of an alcohol, most preferably a lower alkanol such as methanol. This compound can be made by the following two-step reaction:

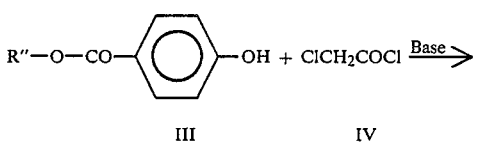

(1)

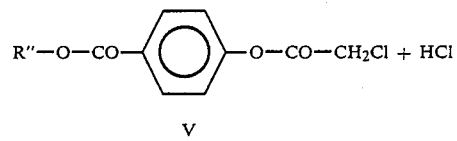

$$III + V \xrightarrow{Base} II + HCl \qquad (2)$$

A base such as triethylamine is used as a hydrogen chloride acceptor. This is an illustration of adding another aromatic moiety to the starting reactant (a) and is also illustrative of the optional aspect of the invention wherein the copolyester contains the divalent unit —Ph—CO—O—, identified as "(C)", above.

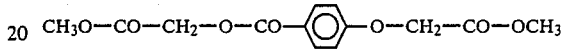

VI.

Compound VI is prepared by reacting two moles of the methyl ester of chloroacetic acid with one mole of p-hydroxybenzoic acid in the presence of a suitable base. Compound VI can be viewed as being a glycolic acid ester of CMB, and is an illustration of, in effect, pre-reacting (a) with (c).

Preparation of Base Polyester

The base polyesters can be produced by an ester exchange or esterification reaction between a dihydric alcohol of Formula VII:

VII and a compound of Formula VIII:

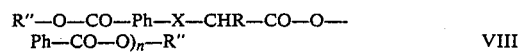

VIII wherein G, Ph, X, R, and R" have the meanings set forth above, and wherein n is a number having a value of 0 or 1.

The dihydric alcohols that can be employed to produce the base polyesters, which can be used singly or in mixtures, include $C_2$ to $C_6$ alkylene glycols such as ethylene glycol, 1,2- and 1,3-propylene glycol, 1,4-butylene glycol, 1,6-hexylene glycol, and the like; polyalkylene glycols such as diethylene glycol, triethylene glycol, poly(oxytetramethylene)glycol, and the like; cycloaliphatic diols such as 1,4-cyclohexanedimethanol, and the like; and aromatic dihydric alcohols such as 1,4-bis(2-hydroxyethoxy)benzene, and the like. The alkylene glycols and polyalkylene glycols are preferred. Ethylene glycol is most preferred.

The compounds of Formula VIII are preferably lower alkyl diesters such as the dimethyl diesters, because they are the most convenient to use in a transesterification reaction. The corresponding half esters or diacids can also be used, if desired, but are usually not preferred. Specific illustrative diesters (or acids) of Formula XV include the dimethyl ester of 4-(carboxymethoxy)benzoic acid, the dimethyl ester of 4-(carboxymethylthio)benzoic acid, the dimethyl ester of 4-(carboxymethylsulfonyl)benzoic acid, the dimethyl ester of 3-(carboxymethoxy)benzoic acid, the dimethyl ester of 2-(carboxymethoxy)benzoic acid, the compound of Formula II, above, and the like.

In place of or in addition to the esters of Formula VIII, the compound identified above as VI (or the thio or sulfonyl analogs) can be employed.

The dihydric alcohol and the diester (or half ester or diacid) are usually reacted in proportions of from about 1.1 to about 4 moles of dihydric alcohol per mole of diester (or half ester or diacid).

A catalytically effective amount of an esterification or transesterification catalyst is used in the reaction. While the reaction would proceed with a wide variety of such catalysts, as a practical matter because the polymers of the invention are intended for use in absorbable products, biologically acceptable catalysts are preferably used in very small amounts. Specific examples of such catalysts are stannous octoate and dibutyltin oxide. Illustrative proportions are from about 3000 to about 30,000, and preferably about 5000 to about 20,000 moles of monomer (i.e., moles of the compound of Formula VIII) per mole of catalyst.

Examples 2-10, below, illustrate the production of the base polyesters of the invention:

EXAMPLES 2-10

Preparation of polyester of ethylene glycol and 4-(carboxymethoxy)benzoic acid

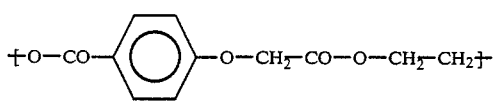

A flame dried, mechanically stirred 100 milliliter glass reactor (suitable for polycondensation reactions) is charged with 22.42 grams (0.1 mole) of the dimethyl ester of 4-(carboxymethoxy)benzoic acid ("CMB"), 15.52 grams (0.25 mole) of ethylene glycol, and 3.73 milligrams of dibutyltin oxide. The contents of the reaction flask are melted at 160° C., in an oil bath under nitrogen. The temperature of the oil bath is raised to 190° C. in 1-2 hours and is maintained at 190° C. for 2 hours, and then 2 hours at 210° C. under nitrogen, during which time the methanol formed is collected. The reactor is allowed to cool to room temperature overnight. The next day, the reaction flask is heated slowly under reduced pressure (0.05-1.0 mm) to 210° C. within 2-3 hours, and is maintained for 4 hours at 210° C., during which time the distillates are collected. The polymer is isolated, ground, and dried in a vacuum oven at room temperature. The resulting polymer has an inherent viscosity ("IV") of 0.69 dl/g in hexafluoroisopropyl alcohol ("HFIP") at 25° C. and at 0.1 g/dl concentration.

Several other polyesters were made by procedures analagous to that described above from varying proportions of CMB to ethylene glycol ("EG"), using either stannous octoate or dibutyltin oxide as the catalyst. Table I, below, displays the mole ratios of the monomers, identity and proportion of catalyst (expressed in moles of CMB per mole of catalyst), and the inherent viscosities, of the polymers.

TABLE I

| Example No. | Mole Ratio of CMB/EG | Catalyst | IV, dl/gm in HFIP |
|---|---|---|---|
| 2 | 1:2.5 | 6667/1 SnBu₂O | 0.69 |
| 3 | 1:2.0 | 6667/1 | 0.19 |
| 4 | 1:2.5 | Sn(Oct)₂ 13,900/1 SnBu₂O | 0.18 |
| 5 | 1:2.5 | 13,900/1 SnBu₂O | 0.30 |
| 6 | 1:2.5 | 13,900/1 SnBu₂O | 0.43 |
| 7 | 1:2.5 | 6667/1 SnBu₂O | 0.51 |
| 8 | 1:2.5 | 10,000/1 SnBu₂O | 0.41 |
| 9 | 1:2.5 | 6667/1 SnBu₂O | 0.62 |
| 10 | 1:2.5 | 6667/1 SnBu₂O | 0.51 |

The base polyesters are essentially noncrystalline materials, or display low levels of crystallinity, having molecular weights in excess of about 5000, and having inherent viscosities of at least about 0.2 dl/gm, tested at a concentration of 0.1 gm/dl in hexafluoroisopropyl alcohol at 25° C.

Preparation of Copolyester

The copolyesters of the invention are produced by reacting the base polyester with a glycolide. The generic term "glycolide" is intended to include the cyclic ester dimer of glycolic acid and/or lactic acid.

The coesterification reaction is preferably carried out by dissolving the polyester in a glycolide, and then subjecting the reaction mixture to elevated temperature for a period of time sufficient to produce the copolyester of the invention. An additional esterification catalyst system may be added for this second polymerization, or the initial catalyst that remains in the reaction mixture from the preparation of the base polyester may be sufficient to catalyze the reaction.

The proportion of polyester to glycolide is selected so that the copolyester will be both absorbable and will be able to withstand radiation sterilization while still maintaining a useful level of physical and biological properties. Within these constraints, typical proportions are from about 1 to about 70 parts, by weight, of base polyester per 100 parts of glycolide, and preferably from about 5 to about 34 parts, by weight, per 100 parts of glycolide.

The following Examples 11-16 illustrate the preparation of the copolyester:

EXAMPLES 11-16

Preparation of copolyester with glycolide

The copolyester will have a molecular weight such that it is normally solid (i.e., solid at 25°-30° C.), and preferably so that it is fiber forming. The inherent viscosity of the copolyester will be above about 0.7 dl/g, and preferably above about 1.1 dl/g, measured at 0.1 g/dl in HFIP at 25° C.

The copolyesters in these Examples 11-16 comprise the repeating divalent units:

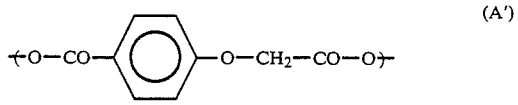

(A')

-continued

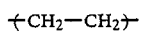 (B')

and

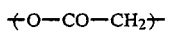 (D')

These copolyesters are made by polymerizing a mixture of a polyester as described in Examples 2–8 and glycolide in the presence of a suitable catalyst such as stannous octoate or dibutyltin oxide. A specific example of such polymerization is given below:

A flame dried 100 milliliter round bottom one neck flask is charged under dry nitrogen with 4.39 grams of the finely divided polyester of Example 2 (which already contains dibutyltin oxide catalyst) and dried 8 hrs/50° C./0.1 mm. To the same flask, after drying, 20.61 grams of glycolide is charged and then the flask is fitted with a mechanical stirrer. The reactor is purged and vented with nitrogen and immersed in a silicone oil bath. The mixture is heated to and maintained at about 100° C. to melt the glycolide and to start the dissolution of polyester in glycolide. The polyester is not readily soluble in glycolide at 100° C. The temperature of the oil bath is raised quickly to 220° C. to improve the dissolution process. This heating process helps to dissolve the polyester in glycolide. The reaction temperature is maintained at 225°–230° C. for 2 hours. The mechanical stirring is discontinued after 30–45 minutes at 225°–230° C. because of the viscous nature of the reaction mass. The polymer is isolated, ground, and dried 16 hrs/110° C./0.1 mm to remove any unreacted glycolide. The resulting polymer has a melting range of about 210°–217° C. and an inherent viscosity of about 1.2 dl/g. at 25° C. and a concentration of 0.1 g/dl in hexafluoroisopropyl alcohol.

By procedures analogous to that described above, several copolyesters were made by reacting glycolide with the polyester of Example 2 (unless otherwise indicated). Table II, below, displays the mole ratio of glycolide to polyester (i.e, moles of glycolide per unit of diacid/glycol in the base polyester), the proportion of catalyst (moles of glycolide unit per mole of catalyst), the inherent viscosity, and the melting point (or range), of the copolyester.

TABLE II

| Example No. | Mole ratio of Polyester/ Glycolide | Catalyst Ratio, $Bu_2SnO$ | I.V., dl/gm in HFIP | M.P., °C. |
|---|---|---|---|---|
| 11 | 10/90 | 60,000/1 | 1.17 | 210–217 |
| 12 | 10/90 (Polyester of Ex. 4) | 125,000/1 | 0.70 | 212–218 |
| 13 | 10/90 (Polyester of Ex. 5) | 125,000/1 | 1.02 | 217–227 |
| 14 | 10/90 | 60,000/1 | 1.03 | 218–229 |
| 15 | 7/93 | 88,500/1 | 1.18 | 223–227 |
| 16 | 12/88 | 48,890/1 | 0.97 | 207–216 |

The para isomers, i.e., the copolyesters wherein Ph in the divalent units "(A)" and "(C)" is 1,4-phenylene, are preferred for the production of fibrous products such as sterile surgical sutures (which may be attached to a needle at one or both ends, in the usual manner), and for the production of other products such as ligating clips that contain sections that require stable orientation, surgical staples, and absorbable meshes. The copolyesters of the invention can be used in powdered form as absorbable fillers in partially or fully absorbable implants or prosthetic devices. The copolyesters can also be used to make molded prosthetic devices or implants.

The following Example 17 illustrates the production of sterile filaments, useful as surgical sutures, from the copolyester of Example 11:

EXAMPLE 17

The copolymer of Example 11 is melt spun into monofilament and annealed at 65° C./12 hrs; dried 16 hrs/50° C./0.7 mm, and Cobalt-60 sterilized. The fiber properties of these monofilaments are shown below in Table III. The Cobalt-60 sterilization did not substantially affect the tensile properties of the monofilament. The fiber is hydrolyzed within 34 days at 50° C. in 7.27 pH buffer solution; thereby indicating that it will be absorbable.

TABLE III

| Properties | Fiber Properties of Copolymer | | | |
|---|---|---|---|---|
| | Before annealing | After annealing at 65° C./12 hr. | After Drying at 50° C./16 h/0.7 mm | After $60_{Co}$ |
| Diameter (mils) | 6.8 | 6.4 | 6.3 | 6.1 |
| Straight Tensile (psi) | 79,025 | 96,400 | — | 89,600 |
| Knot Tensile (psi) | 56,722 | — | 71,200 | 67,700 |
| % Elongation | 50 | 22 | — | 34 |
| Initial Modulus (psi) | 704,424 | 1,418,333 | — | 1,545,000 |

EXAMPLES 18–20

Preparation of dimethyl ester of 4-(carboxymethoxy)benzoic acid (Larger batch size)

3500 Grams (23 moles) of methyl p-hydroxybenzoate, 2996 grams (27.6 moles) of methyl chloroacetate, and 4911 milliliters of anhydrous methanol, are charged into a 22-liter, 3 neck, round bottom flask fitted with an addition funnel, nitrogen inlet, a mechanical stirrer, a reflux condenser, thermometer, and heating mantle. The reaction mixture is refluxed for 30–60 minutes. 4969 Grams of sodium methoxide solution (25% by weight in anhydrous methanol or 23 moles of sodium methoxide) is added dropwise in 1.5–2.5 hours at reflux. After the addition is completed the reaction mixture is refluxed for 16 hours under nitrogen purge. 12 Milliliters of glacial acetic acid is added. Then it is hot filtered to remove the precipitated sodium chloride. Upon cooling the mother liquor, colorless crystalline material is formed. The crystals are filtered, dried and then recrystallized twice from anhydrous methanol using 1.25–1.50 milliliters per gram of dried product. The product has a melting point of 93°–94° C. with an overall yield of 74.7%.

Two other batches are run under analogous conditions. Table IV, below, displays the results:

TABLE IV

| Example No. | Yield, % | M. P. | Appearance |
|---|---|---|---|
| 18 | 74.7 | 93°–94° C. | Colorless crystals |
| 19 | 79 | 93°–94° C. | Colorless crystals |
| 20 | 63.6 | 93°–94° C. | Colorless crystals |

The structure of the monomer is confirmed by elemental analysis and NMR.

EXAMPLES 21–22

Preparation of base polyester—Larger Batch Size

A thoroughly dried, mechanically stirred 1.5 gallon stainless steel reactor suitable for polycondensation reactions is charged with 2018 grams (9.0 moles) of the dimethyl ester of 4-(carboxymethoxy)benzoic acid (CMB), 1676 grams (27.0 moles) of ethylene glycol, and 0.3360 grams of dibutyltin oxide. The contents of the reactor are heated to 190° C. within 2 hours. The reaction temperature is maintained at 190°–200° C. for 2 hours and 200°–210° C. for 2–6 hours, during which time the theoretical quantity of formed methanol is collected. The reactor is allowed to cool to room temperature overnight. The next day, the reactor is heated slowly under reduced pressure (0.05–1.0 mm) to 200° C. The reactor is maintained at 200°–220° C./0.05–1.0 mm for 8–16 hours, during which time the ethylene glycol formed is removed. The inherent viscosities (I.V.) are measured at regular intervals, and the reaction is terminated when the desired I.V. is obtained.

Table V, below, displays the results for two batches.

TABLE V

| Example | Mole Ratio of CMB/EG | Catalyst $Bu_2SnO$ | I.V., dl/gm in HFIP |
|---|---|---|---|
| 21 | 1:3.0 | 6667/1 | 0.51 |
| 22 | 1:3.0 | 6667/1 | 0.61 |

EXAMPLE 23

Preparation of copolyester with glycolide (Large Batch)

A thoroughly dried, mechanically stirred 1.5 gallon stainless steel reactor is charged with 329.69 grams of the polyester of Example 21 (dried 16 hrs./50° C./0.1 mm.) and 1670.3 grams of glycolide. The reactor is purged and vented with nitrogen. The mixture is heated to 100° C. and maintained at 100°–120° C. for 30–60 minutes without stirring. While stirring the reactor is heated stepwise to 150° C., 170° C., 190° C., and to 210° C. within 1 hour and then maintained 2 hours at 210° C. under nitrogen. The polymer is isolated, ground, and dried 16 hrs./110° C./0.1 mm to remove unreacted glycolide.

Table VI, below, displays the results, along with the results of the preparation of three additional lab sized batches (Examples 24–26) of copolyester (from the polyester of Example 9).

TABLE VI

| Example No. | Mole Ratio Polyester to Glycolide | Catalyst Ratio, $Bu_2SnO$ | I. V., dl/gm in HFIP | m. p., °C. |
|---|---|---|---|---|
| 23 | 10/90 | 60,000/1 | 1.09 | 211–221 |
| 24 | 10/90 | 60,000/1 | 1.53 | 212–218 |
| 25 | 10/90 | 60,000/1 | 1.40 | 208–216 |
| 26 | 10/90 | 60,000/1 | 1.26 | 206–210 |

Monofilaments were extruded from the copolyesters of Examples 23, 24, and 25. Table VII, below, displays the extrusion temperatures, drawing conditions, and representative physical properties of these monofilaments.

TABLE VII

Properties of Monofilaments

| | Example No. 24 | | Example No. 25 | | Example No. 23 | |
|---|---|---|---|---|---|---|
| Inherent viscosity (I.V.) | 1.53 | | 1.40 | | 1.09 | |
| Extrusion temp., °C. | 235 | | 245 | | 240 | |
| Orientation Number | 1 | 2 | 1 | 2 | 1 | 2 |
| First Draw | 5X at 51° C. | 5X at 59° C. | 5X at 51° C. | 5.5X at 56° C. | 6X at 55° C. | 5X at 53° C. |
| Second Draw | 1.2X at 72° C. | 1.2X at 80° C. | 1.3X at 70° C. | — | — | 1.3X at 70° C. |
| Physical Properties | | | | | | |
| Diameter, (mils) | 7.2 | 7.4 | 6.8 | 7.5 | 6.8 | 7.0 |
| Straight Tensile, psi $\times 10^{-3}$ | 134 | 77.9 | 118.7 | 86.5 | 107.9 | 155.3 |
| Knot Tensile, psi $\times 10^{-3}$ | 98.9 | 67.4 | 92.5 | 55.7 | 69.9 | 88.7 |
| % Elongation | 31.0 | 58.8 | 28.0 | 62.4 | 67.6 | 26.1 |
| Modulus, psi $\times 10^{-6}$ | 1.92 | 1.29 | 1.56 | 0.8 | 0.97 | 2.22 |

Physical properties of the monofilament of Example 24 prior to and after annealing (under tension) and after exposure to a 2.5 Mrad does of gamma radiation, are displayed in Table VIII:

TABLE VIII

| | Prior to Annealing | After Annealing (9 hrs./113° C.) and Drying (72 hrs./50° C.) | After Annealing and Gamma Radiation |
|---|---|---|---|
| Diameter, (mils) | 7.2 | 7.2 | 7.4 |
| Straight Tensile Strength, (psi) | 134,097 | 142,874 | 127,878 |
| Knot Tensile Strength, (psi) | 98,976 | 100,535 | 95,341 |
| Elongation at Break, (%) | 31 | 20.9 | 20.3 |
| Young's Modulus, psi | 1,920,542 | 1,809,840 | 1,565,101 |

Breaking Strength Retention

The breaking strength of a sample is determined by implanting two strands of a sample in the dorsal subcutis of each of twelve (12) Long-Evans rats. Thus 24 strands of each sample are implanted corresponding to the three implantation periods; eight examples of each sample for each of the periods. The periods of in vivo residence are 7, 14, and 21 days. The ratio of the mean value (of 8 determinations) of the breaking strength (determined with an Instron Tensile tester in accordance with standard testing procedure) at each period to the mean value (of 8 determinations) obtained for the sample prior to implantation constitutes its breaking strength retention for that period.

The results of the breaking strength retention tests for the monofilament of Example 24 are displayed in Table IX:

TABLE IX

Breaking Strength Retention of Experimental Monofilaments

| Example 24 | Time in Days | | | |
|---|---|---|---|---|
| | 0 | 7 | 14 | 21 |
| Non-Irradiated, lbs- | 5.8 | — | 3.7 | 2 |
| % Retention | 100 | — | 64.7 | 34 |
| Irradiated, lbs- | 6 | — | 2.6 | 0.14 |
| % Retention | 100 | — | 43 | 2.3 |

What is claimed is:

1. A surgical suture comprising a drawn and oriented fiber of an absorbable, radiation sterilizable, normally solid copolyester comprising the repeating divalent units of the formula:

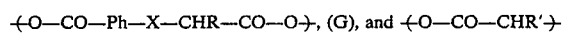, (G), and 

wherein Ph represents 1,2-, 1,3-, or 1,4-phenylene, or lower alkyl- or lower alkoxy-substituted phenylene, wherein R represents hydrogen, lower alkyl, phenyl, or benzyl, wherein X represents oxy, thio, or sulfonyl, wherein G represents the residue after removal of the alcohol groups of a dihydric alcohol, wherein R' represents hydrogen or methyl, and wherein said divalent units are bonded to each other through ester groups contained in said units.

2. The suture of claim 1 wherein Ph is 1,4-phenylene.

3. The suture of claim 2 wherein X is oxy and R is hydrogen.

4. The suture of claim 2 wherein G represents alkylene of from two to six carbon atoms.

5. The suture of claim 3 wherein G represents alkylene of from two to six carbon atoms.

6. The suture of claim 2 wherein G represents ethylene.

7. The suture of claim 3 wherein G represents ethylene.

8. The suture of claim 2 wherein R' represents hydrogen.

9. The suture of claim 3 wherein R' represents hydrogen.

10. The suture of claim 1 wherein said polymer comprises repeating divalent units of the formulas:

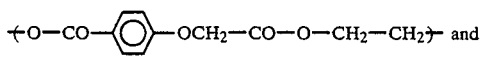 and

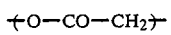

11. The suture of claim 1 wherein the —O—CO—CHR'— moiety constitutes from about 59 to about 99 weight percent of the polymer.

12. The suture of claim 2 wherein the —O—CO—CHR'— moiety constitutes from about 59 to about 99 weight percent of the polymer.

13. The suture of claim 3 wherein the —O—CO—CHR'— moiety constitutes from about 59 to about 99 weight percent of the polymer.

14. The suture of claim 10 wherein the —O—CO—CHR'— moiety constitutes from about 59 to about 99 weight percent of the polymer.

15. The suture of claim 2 in sterile condition.

16. The suture of claim 3 in sterile condition.

17. The suture of claim 10 in sterile condition.

18. The suture of claim 15 having a needle attached to at least one end of the suture.

19. The suture of claim 1 wherein said polymer additionally contains the divalent unit of the formula:

—Ph—CO—O— wherein Ph is as defined in claim 1.

20. The suture of claim 1 wherein said polymer is the product of a reaction between (a) glycolide, lactide, or mixture thereof, and (b) a polyester comprising the repeating divalent unit of the formula:

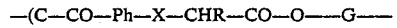

wherein Ph, X, R, and G have the meanings set forth in claim 1, said reaction being carried out in the presence of an esterification or transesterification catalyst.

21. The suture of claim 24 wherein said polymer is the product of a reaction between (a) glycolide, lactide, or mixture thereof, and (b) a polyester comprising the repeating divalent unit of the formula:

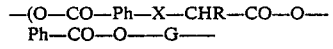

wherein Ph, X, R, and G have the meanings set forth in claim 1, said reaction being carried out in the presence of an esterification or transesterification catalyst.

22. The suture of claim 23 wherein Ph is 1,4-phenylene, X is oxy, R is hydrogen, and G is ethylene.

23. The suture of claim 1 wherein Ph is 1,4-phenylene, X is oxy, R is hydrogen, and G is ethylene.

* * * * *

UNITED STATES PATENT AND TRADEMARK OFFICE
CERTIFICATE OF CORRECTION

PATENT NO. : 4,532,928

DATED : August 6, 1985

INVENTOR(S) : Rao S. Bezwada et al.

It is certified that error appears in the above-identified patent and that said Letters Patent is hereby corrected as shown below:

Column 12, line 33, "-(C-CO-Ph-X-CHR-CO-O-G-" should read -- -(O-CO-Ph-X-CHR-CO-O-G- --.

Signed and Sealed this

Twelfth Day of November 1985

[SEAL]

Attest:

Attesting Officer

DONALD J. QUIGG

Commissioner of Patents and Trademarks